US00PP35256P2

(12) United States Plant Patent
Eggleton et al.

(10) Patent No.: US PP35,256 P2
(45) Date of Patent: Jul. 4, 2023

(54) ***LAVANDULA* PLANT NAMED 'IB6101'**

(50) Latin Name: ***Lavandula stoechas* spp. *pedunculata***
Varietal Denomination: IB6101

(71) Applicant: PLANT GROWERS AUSTRALIA PTY. LTD., Wonga Park (AU)

(72) Inventors: Steven Eggleton, Wonga Park (AU); Howard Bentley, Wonga Park (AU)

(73) Assignee: PLANT GROWERS AUSTRALIA PTY. LTD., Wonga Park (AU)

( * ) Notice: Subject to any disclaimer, the term of this patent is extended or adjusted under 35 U.S.C. 154(b) by 0 days.

(21) Appl. No.: 17/976,777

(22) Filed: Oct. 29, 2022

Related U.S. Application Data

(60) Provisional application No. 63/340,422, filed on May 10, 2022.

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — C. Anne Whealy

(57) ABSTRACT

A new and distinct cultivar of *Lavandula* plant named 'IB6101', characterized by its relatively tall and upright plant habit; freely branching growth habit, dense and bushy appearance; freely flowering habit; white-colored flowers with large white-colored sterile flower bracts arranged on short terminal spikes; and good garden performance.

1 Drawing Sheet

Botanical designation: *Lavandula stoechas* spp. *pedunculata.*

Cultivar denomination: 'IB6101'.

BACKGROUND OF THE INVENTION

The present invention relates to a new and distinct *Lavandula* plant, botanically known as *Lavandula stoechas pedunculata*, commonly referred to as French Lavender and hereinafter referred to by the name 'IB6101'.

The new *Lavandula* plant is a product of a planned breeding program conducted by the Inventors in Wonga Park, Victoria, Australia. The objective of the breeding program was to develop new dense and freely-flowering *Lavandula* plants with attractive plant form and flower coloration and good garden performance.

The new *Lavandula* plant originated from a self-pollination in October, 2015 of *Lavandula stoechas pedunculata* 'FW Spellbound', disclosed in U.S. Plant Pat. No. 31,641. The new *Lavandula* plant was discovered and selected by the Inventors as a single flowering plant within the progeny of the stated self-pollination in a controlled greenhouse environment in Wonga Park, Victoria, Australia in October, 2016.

Asexual reproduction of the new *Lavandula* plant by softwood terminal cuttings in a controlled greenhouse environment in Wonga Park, Victoria, Australia since October, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'IB6101' as a new and distinct *Lavandula* plant:

1. Relatively tall and upright plant habit.
2. Freely branching growth habit, dense and bushy appearance.
3. Freely flowering habit.
4. White-colored flowers with large white-colored sterile flower bracts arranged on short terminal spikes.
5. Good garden performance.

Plants of the new *Lavandula* differ primarily from plants of the parent, 'FW Spellbound', in the following characteristics:

1. Plants of the new *Lavandula* and 'FW Spellbound' differ in flower color as flowers of plants of the new *Lavandula* are white in color whereas flowers of plants of 'FW Spellbound' are dark greyed purple in color.
2. Plants of the new *Lavandula* and 'FW Spellbound' differ in sterile flower bract color as flowers of plants of the new *Lavandula* have white-colored sterile flower bracts whereas flowers of plants of 'FW Spellbound' have purple violet-colored sterile flower bracts.

Plants of the new *Lavandula* differ primarily from plants of *Lavandula stoechas pedunculata*, 'IB61003', disclosed in a U.S. Plant Patent application filed concurrently, in the following characteristics:

1. Plants of the new *Lavandula* are taller than plants of 'IB61003'.
2. Plants of the new *Lavandula* and 'IB61003' differ in flower color as flowers of plants of the new *Lavandula* are white in color whereas flowers of plants of 'IB61003' are light pink in color.

3. Plants of the new *Lavandula* have larger sterile flower bracts than plants of 'IB61003'.
4. Plants of the new *Lavandula* and 'IB61003' differ in sterile flower bract color as flowers of plants of the new *Lavandula* have white-colored sterile flower bracts whereas flowers of plants of 'IB61003' have light pink-colored sterile flower bracts.

Plants of the new *Lavandula* can be compared to plants of *Lavandula stoechas pedunculata* 'FW Whimsical', disclosed in U.S. Plant Pat. No. 31,679. In side by side comparisons, plants of the new *Lavandula* and 'FW Whimsical' differ primarily in the following characteristics:

1. Plants of the new *Lavandula* are more upright than and not as outwardly spreading as plants of 'FW Whimsical'.
2. Plants of the new *Lavandula* are denser than plants of 'FW Whimsical'.
3. Plants of the new *Lavandula* have shorter sterile flower bracts than plants of 'FW Whimsical'.
4. Plants of the new *Lavandula* and 'FW Whimsical' differ in sterile flower bract color as flowers of plants of the new *Lavandula* have white-colored sterile flower bracts whereas flowers of plants of 'FW Whimsical' have light red purple-colored sterile flower bracts.

Plants of the new *Lavandula* can also be compared to plants of the *Lavandula stoechas* 'Sweetberry Ruffles', disclosed in U.S. Plant Pat. No. 22,447. In side-by-side comparisons, plants of the new *Lavandula* differ primarily from plants of 'Sweetberry Ruffles' in the following characteristics:

1. Plants of the new *Lavandula* and 'Sweetberry Ruffles' differ in flower color as flowers of plants of the new *Lavandula* are white in color whereas flowers of plants of 'Sweetberry Ruffles' are red purple in color.
2. Plants of the new *Lavandula* have narrower sterile flower bracts than plants of 'Sweetberry Ruffles'.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph is a side perspective view of a typical flowering plant of 'IB6101' grown in a container.

DETAILED BOTANICAL DESCRIPTION

The aforementioned photograph and following observations, measurements and values describe plants grown during the summer in an outdoor nursery in Fort Worth, Tex. and under cultural practices typical of commercial *Lavandula* production. During the production of the plants, day temperatures ranged from 35° C. to 40° C. and night temperatures ranged from 24° C. to 35° C. Plants were six months old when the photograph and the description were taken. In the description, color references are made to The Royal Horticultural Society Colour Chart, 2015 Edition, except where general terms of ordinary dictionary significance are used.

Botanical classification: *Lavandula stoechas pedunculata* 'IB6101'.

Parentage:

*Female, or seed, parent.*—*Lavandula stoechas pedunculata* 'FW Spellbound', disclosed in U.S. Plant Pat. No. 31,641.

*Male, or pollen, parent.*—*Lavandula stoechas pedunculata* 'FW Spellbound', disclosed in U.S. Plant Pat. No. 31,641.

Propagation:

*Type.*—Terminal softwood vegetative cuttings.

*Time to initiate roots, summer.*—About ten days at temperatures about 24° C.

*Time to initiate roots, winter.*—About twelve days at temperatures about 21° C.

*Time to produce a rooted young plant, summer.*—About 24 to 28 days at temperatures ranging from 23° C. to 26° C.

*Time to produce a rooted young plant, winter.*—About 35 to 40 days at temperatures ranging from 15° C. to 18° C.

*Root description.*—Fine, fibrous; typically white to light brown in color, actual color of the roots is dependent on substrate composition, water quality, fertilizer type and formulation.

*Rooting habit.*—Freely branching; medium density.

Plant description:

*Plant and growth habit.*—Herbaceous perennial; relatively tall and upright plant habit; roughly columnar in overall shape; moderately vigorous growth habit; relatively rapid growth rate; flowers arranged in verticillasters on terminal spikes; freely branching habit, dense and bushy appearance.

*Plant height, soil level to top of foliar plane.*—About 23.5 cm.

*Plant height, soil level to top of floral plane.*—About 27.75 cm.

*Plant width.*—About 21.4 cm.

*Lateral branch description.*—Quantity per plant: About eight to nine primary lateral branches each with potentially two secondary branches developing at every node during the flowering season. Length: About 16 cm. Diameter: About 1.25 mm. Internode length: About 1.6 cm. Strength: Moderately strong; flexible. Aspect: Mostly upright to slightly outwardly. Texture and luster: Densely tomentose; slightly glossy. Color, developing: Close to 144A to 144B. Color, developed: Close to 144B to 144C; if woody, close to 199A.

*Leaf description.*—Arrangement: Opposite, simple; sessile. Length, largest leaves: About 3.8 cm. Width, largest leaves: About 5 mm. Shape: Linear. Apex: Acute. Base: Cuneate. Margin: Entire; slightly to moderately revolute. Texture and luster, upper and lower surfaces: Densely pubescent; matte. Fragrance: Strongly aromatic, pungent. Venation pattern: Pinnate. Color: Developing leaves, upper surface: Close to 137B. Developing leaves, lower surface: Close to 138A. Fully expanded leaves, upper surface: Close to NN137B to NN137C; venation, close to 144A. Fully expanded leaves, lower surface: Close to 137B; venation, close to 138A.

Flower description:

*Flower type, arrangement and habit.*—Small single salverform flowers arranged in verticillasters on terminal cylindrical spikes; freely flowering habit with about 60 to 80 flowers developing in six to eight whorls per inflorescence and numerous inflorescences developing per plant during the flowering season; flowers with two-lobed upper lip and three-lobed lower lip; flowers face mostly outwardly on the spike.

*Natural flowering season.*—Relatively long flowering period; continuous from late winter to late spring/early summer in Australia.

*Flower longevity on the plant.*—Inflorescences last about one month on the plant; flowers not persistent.

*Fragrance.*—Resinous, pungent.

*Flower buds.*—Length: About 7 mm. Diameter: About 3 mm. Shape: Ovoid. Color: Close to 143A to 143B.

*Inflorescence height.*—About 2.25 cm, excluding terminal bracts.

*Inflorescence diameter.*—About 1 cm, excluding terminal bracts.

*Flower diameter.*—About 2.5 mm.

*Flower depth (height).*—About 4 mm, including tube.

*Flower tube length.*—About 2 mm.

*Flower tube diameter.*—Less than 1 mm.

*Petals.*—Quantity and arrangement: Upper lip, two-lobed and lower lip, three-lobed. Length, upper and lower lips: About 1.9 mm. Width, upper and lower lips: About 1.4 mm. Shape, upper lip: Obovate. Shape, lower lip: Ovate. Apex, upper and lower lips: Obtuse, rounded. Margin, upper and lower lips: Entire; slightly undulate. Texture and luster, upper (inner) surface, upper and lower lips: Smooth, glabrous; slightly velvety; matte. Texture and luster, lower (outer) surface, upper and lower lips: Smooth, glabrous; slightly velvety; slightly glossy. Color, upper and lower lips: When opening and fully opened, upper (inner) and lower (outer) surfaces: Close to NN155D.

*Basal flower bracts.*—Quantity and arrangement: Each group of flowers is subtended by a single basal flower bract. Length: About 9 mm. Width: About 1 cm. Shape: Cordate. Apex: Long cuspidate. Base: Truncate with cordate tendencies. Margin: Entire. Texture, upper and lower surfaces: Smooth, glabrous. Color, upper and lower surfaces: Translucent, close to NN155D with venation, close to 143A.

*Sterile flower bracts.*—Quantity and arrangement: About four to six sterile flower bracts at apex of spike. Length: About 3.75 cm. Width: About 1.25 cm. Shape: Oblong; ruffled appearance. Apex: Acute. Base: Cuneate. Margin: Entire; undulate. Texture and luster, upper and lower surfaces: Smooth, glabrous; matte. Color, upper and lower surfaces: Close to NN155D; main vein, close to 144A to 144B; color does not change with subsequent development.

*Sepals.*—Quantity and arrangement: Five, fused into a campanulate tube. Calyx length: About 5 mm. Calyx diameter: About 3 mm. Shape: Lanceolate. Apex: Acute. Margin: Entire. Texture and luster, upper (inner) and lower (outer) surfaces: Densely pubescent; matte. Color, upper (inner) and lower (outer) surfaces: Close to 143A.

*Peduncles.*—Length: About 4.25 cm. Diameter: About 1.5 mm. Aspect: Mostly upright. Strength: Moderately strong to strong; flexible. Texture and luster: Pubescent; matte. Color: Close to 144A.

*Reproductive organs.*—Stamens: Quantity per flower: Four. Anther shape: Reniform. Anther color: Close to 157C. Pollen amount: None observed. Pistils: Quantity per flower: One. Stigma shape: Club-shaped. Stigma color: Close to N79A. Ovary color: Close to 143A to 143B.

*Seeds and fruits.*—To date, seed and fruit production has not been observed on plants of the new *Lavandula*.

Pathogen & pest resistance: To date, plants of the new *Lavandula* have not been observed to be resistant to pathogens and pests common to *Lavandula* plants.

Garden performance: Plants of the new *Lavandula* have exhibited good garden performance and to tolerate rain and wind and temperatures ranging from 0° C. to 42° C.

It is claimed:

1. A new and distinct *Lavandula* plant named 'IB6101' as illustrated and described.

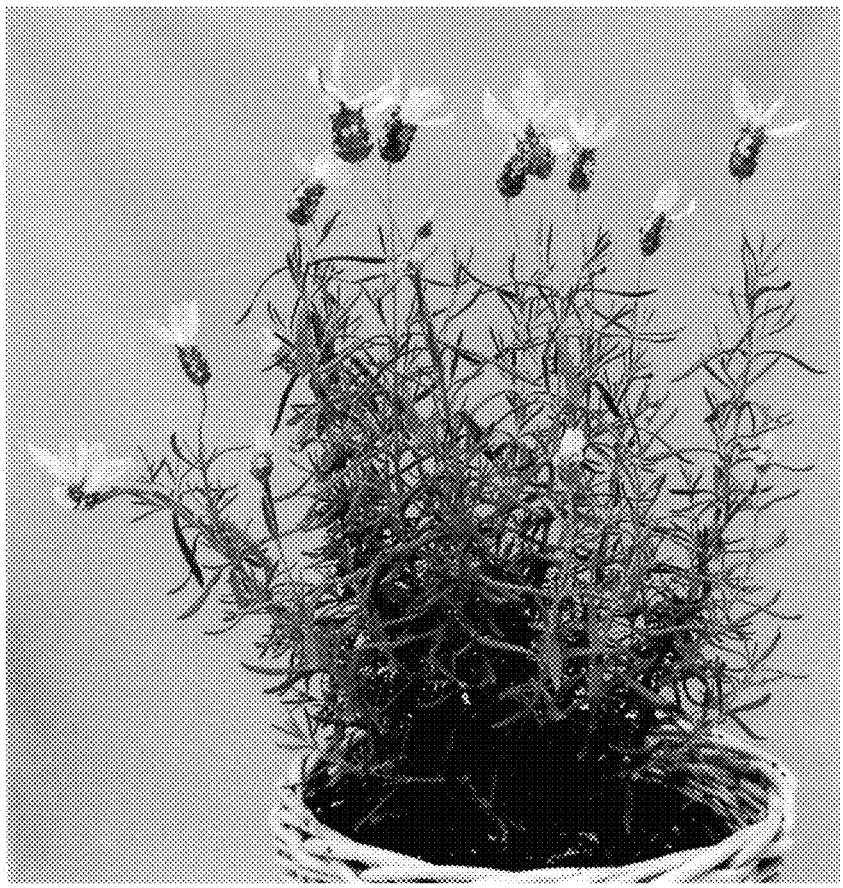

* * * * *